United States Patent [19]
Carretero Gonzalvez et al.

[11] Patent Number: 5,521,310
[45] Date of Patent: May 28, 1996

[54] PROCESS TO OBTAIN BENZOXAZINES TO BE USED FOR THE SYNTHESIS OF OFLOXAZINE, LEVOFLOXAZINE AND DERIVATIVES

[75] Inventors: Juan-Carlos Carretero Gonzalvez; Mercedes Vicioso Sanchez; José-Luis Garcia Ruano, all of Cuevas del Almanzora, Spain

[73] Assignee: Derivados del Etilo, S.A., Cuevas De Almanzora, Spain

[21] Appl. No.: 244,455

[22] PCT Filed: Oct. 6, 1993

[86] PCT No.: PCT/ES93/00080

§ 371 Date: Aug. 31, 1994

§ 102(e) Date: Aug. 31, 1994

[87] PCT Pub. No.: WO94/07873

PCT Pub. Date: Apr. 14, 1994

[30] Foreign Application Priority Data

Oct. 7, 1992 [ES] Spain .................................. 9201983
Oct. 4, 1993 [ES] Spain .................................. 9302080

[51] Int. Cl.[6] .................................................. C07D 498/16
[52] U.S. Cl. .................................................. 544/101; 544/105
[58] Field of Search .................................. 544/101, 105

[56] References Cited

U.S. PATENT DOCUMENTS 4,382,892  5/1983  Hayakawa et al. ...................... 544/101

FOREIGN PATENT DOCUMENTS

| | | |
|---|---|---|
| 0047005 | 3/1982 | European Pat. Off. . |
| 0206283 | 12/1986 | European Pat. Off. . |
| 3522406 | 1/1987 | Germany . |
| 3639465 | 5/1988 | Germany . |
| 1758788 | 7/1992 | Germany . |
| 1444043 | 11/1987 | Japan . |
| 553520 | 3/1986 | Spain . |

Primary Examiner—Yogendra N. Gupta
Attorney, Agent, or Firm—Keck, Mahin & Cate

[57] ABSTRACT

A process to obtain benzoxazines useful for the synthesis of Ofloxazine, Levofloxazine and derivatives. The benzoxacines (I) where Xb is an halogen and $R_1$ is H, alkyl or alkenyl of up to 6 atoms of C or aryl, can be obtained by means of cycling a compound of formula (II) through the reaction with triphenylphosphine and ethyl azodicarboxilate. The compounds of formula (II) can be obtained through the reaction of a compound (III) with an adequate epoxide. Through the use of the adequate chiral epoxide it is possible to obtain the enantiomerically desired intermediate and, therefore and selectively, it is possible to obtain the desired final product with the adequate enantiomeric form without the need to carry out a resolution stage.

The Compounds (I) are useful and key intermediates for the synthesis of the antimicrobials Oflixazine and Levofloxazine.

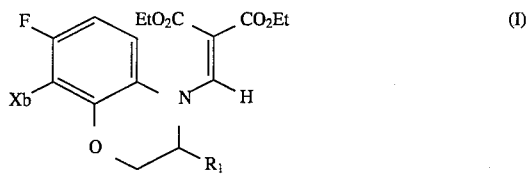

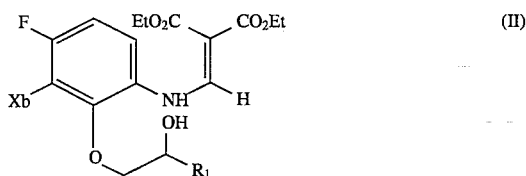

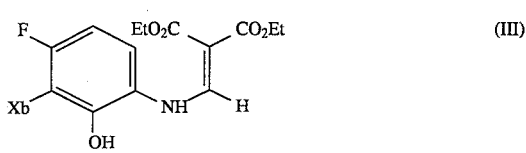

2 Claims, No Drawings

PROCESS TO OBTAIN BENZOXAZINES TO BE USED FOR THE SYNTHESIS OF OFLOXAZINE, LEVOFLOXAZINE AND DERIVATIVES

This invention describes a new process for the synthesis of benzoxazine derivatives of general formula (I)

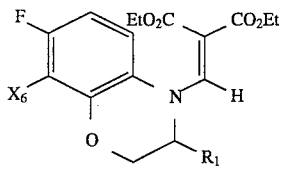

where:
- $R_1$ is H, an alkyl radical of up to 6 carbon atoms, preferably methyl, an alkenyl radical of up to 6 carbon atoms or an aryl group; and
- Xb is an halogen atom.

These compounds of formula (I) are advanced and key intermediates for the commercial synthesis of antibacterial compounds such as the Ofloxazine (racemate) and its enantiomerically pure forms, among them the levofloxacine.

BACKGROUND OF THE INVENTION

The formula of the Ofloxacine [9-fluoro-3-methyl-10-(4-methyl-1-piperazinyl)-7-oxo-2,3 dihydro-7H-pyrid(1,2,3-de) (1,4)-benzoxazine-6-carboxylic acid] is:

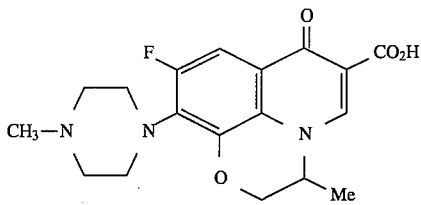

It is described in Patents: Japanese No. 1,444,043; U.S. Pat. No. 4,382,892 and European No. EP-B-0,047,005. The Ofloxazine is an excellent synthetical antimicrobial agent as mentioned in the application for Japanese Patent No. 46986/92 (OPI) which has been marketed in many countries.

The Ofloxazine has an asymmetric carbon atom in position 3 and is normally obtained as racemate through processes already known. However, through the process of this invention, it is possible to directly obtain any of its optically active forms without the need to carry out any resolution stage.

The researches made by the authors of this invention have shown that the 3-(S)- isomer of the Ofloxazine, known as Levofloxazine, has (1) an antimicrobial activity twice higher than that of the racemic thus confirming the statements of European Patent No. EP-A-0,206,283 and (ii) an acute toxicity ($LD_{50}$) weaker than that of the racemic compound which has been determined in mice through intravenous administration. Furthermore, it has been possible to assess that the isomer (R) presents (i) an antimicrobial activity between ten and one hundred times lower than that of the racemic compound and (ii) it has an acute toxicity basically similar to that of such racemic one. Consequently, the (S) form of Ofloxazine (Levofloxazine) presents very interesting properties, such as an increased antimicrobial activity and a reduced toxicity. Therefore it can be assumed that this compound will be—from a pharmaceutical point of view—more useful than the racemic one.

Indeed, it has been possible to determine that the water solubility of both the (R)-Ofloxazine form and the (S)-Ofloxazine form in free form is higher than that of the (R,S) compound and, therefore, it can be used for injectable preparations.

The description of the Ofloxazine and of the Levofloxazine as well as their application to human and veterinary clinics appear in the German Patents No. DE 3522406 A1 and DE 3639465 A1 respectively.

The Spanish Patent No. 553520 describes a process to obtain the Ofloxacine by hydrolysis of the preceding nitrile9-fluorine-3-methyl-10-(4-methyl-1-piperazinyl)-7-oxo-2,3-dihydro-7H-pyrid(1,2,3-de)-(1,4)-benzoxazine-6-carbonitrile.

In general terms, all the synthesis processes of the Ofloxacine and of the Levofloxazine normally used are based on expensive products and call for a resolution stage to separate the pure enantiomers. On the contrary, the procedure of this invention offers the following advantages when compared with the previous technique:

a) direct access to both optically-active enantiomer forms of the Ofloxazine without the need of a resolution stage; and b) the use of an initial product (3,4-difluorineaniline) easier and cheaper than that used in other previous patents (2,3-difluorine-6-nitrophenol).

DETAILED DESCRIPTION OF THE INVENTION

This invention provides a process to prepare bezoxazine derivatives of formula (I):

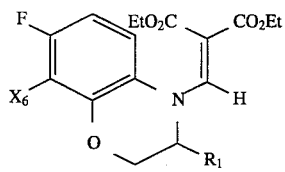

where:
- $R_1$ is H, an alkyl radical of up to 6 carbon atoms, preferably methyl, an alkenyl radical of up to 6 carbon atoms or an aryl group; and
- Xb is an halogen atom, preferably fluorine.

The term "alkyl radical of up to 6 carbon atoms" shall be understood—as used in this description—as any radical derived from a lineal or ramified alkane chain of up to 6 carbon atoms inclusive such as methyl, ethyl, propyl, isopropyl.

Analogically, the term "alkenyl radical of up to 6 carbon atoms" shall be understood as any radical derived from a lineal or ramified alkene chain of up 6 carbon atoms inclusive which has one or more unsaturation degrees in any position of the chain.

Similarly, the term "aryl" shall be understood as a phenyl group, optionally replaced by one or more alkyl groups or one or more halogen atoms.

To carry out the synthesis of the benzoxazines (I) mentioned above, it is necessary to synthesize the oxibenzenes derivatives of general formula (II)

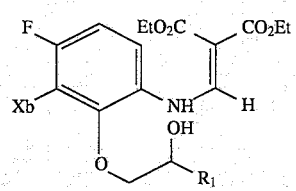

(II)

which can be obtained through the reaction between an epoxide

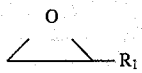

$R_1$ and a compound of formula (III)

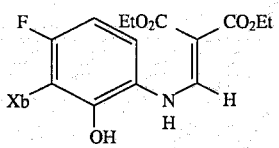

(III)

where, in all formulae considered, $R_1$ and Xb have the meaning described above.

One of the objects of this invention is to obtain this formula (I) intermediates through a new synthetic way which enables to obtain racemic Ofloxazine and its enantiomers. An additional object of this invention is the preparation of these intermediates through a new process for its use in the synthesis of the above-mentioned antimicrobial compounds.

Another object of this invention is the use of racemic or enantiomerically pure epoxides which, in the specific and preferred case of this invention, can be (R,S)-propylene oxide or (R)-propylene oxide in one of the synthesis stages which, in a specific and preferred situation, will enable the preparation of the intermediate (3,4diofluoro-2-(2-hydroxypropoxy)aniline) methylenmalonate of diethyl enantiomerically pure which incorporated into the synthetic route of the Ofloxacina will enable the formation of Levofloxacina without the need of an enantiomer resolution stage.

Now, we will described in detail the synthesis of the compounds of formula (I) offered by this invention as well as those of the Ofloxazine in their racemic and enantiomerically pure forms. The reaction scheme included in this description includes the sequence of the reactions involved in an especially preferred execution of this invention. Specifically, the scheme shows the steps and reactives necessary to obtain the benzoxiazine [6] derivative used as intermediate in the synthesis of the ofloxazine [9]. Other compounds of formula (I) included within the scope of this invention can be easily prepared by an average expert in this field just by making the relevant modifications.

The compounds of formula (I) of this invention can be prepared through the process that, applied to the specific case mentioned above, is described hereafter.

Among the different oxibenzene derivatives of formula (II) that can be obtained through this invention, one of the most important compound groups are the 2,3-difluorine-6-aminopropoxybenzenes of formula [5] shown in the reaction scheme. These compounds can be obtained from the 3,4-difluoroaniline compound which is commercially available.

The 3,4-difluoroaniline compound can be converted into benzoxazine derivatives (identified as compound [6] in the reaction scheme, it corresponds to a compound of formula (I) where Xb is F and $R_1$ is a methyl, and subsequently in Ofloxacine and other quinolones structurally related through a series of reactions that are shown in the attached scheme.

The sequence of reactions is as follows:
a) Protection of the amino group
b) Regioselective orthometalation and reaction with boric compounds
c) Deprotection of the amino group
d) Methylenmalonation of the amino group
e) Formation of the propoxybenzene derivative through the opening of epoxides
f) Cycling to benzoxazine derivatives
g) Formation of the chinoline ring
h) Hydrolysis of the ethyl carboxylate
i) Replacement of fluorine by N-methylpiperazine In this series of reactions, the products obtained can be isolated or purified through already known methods such as: extraction, recrystallization, flash chromatography or a combination thereof.

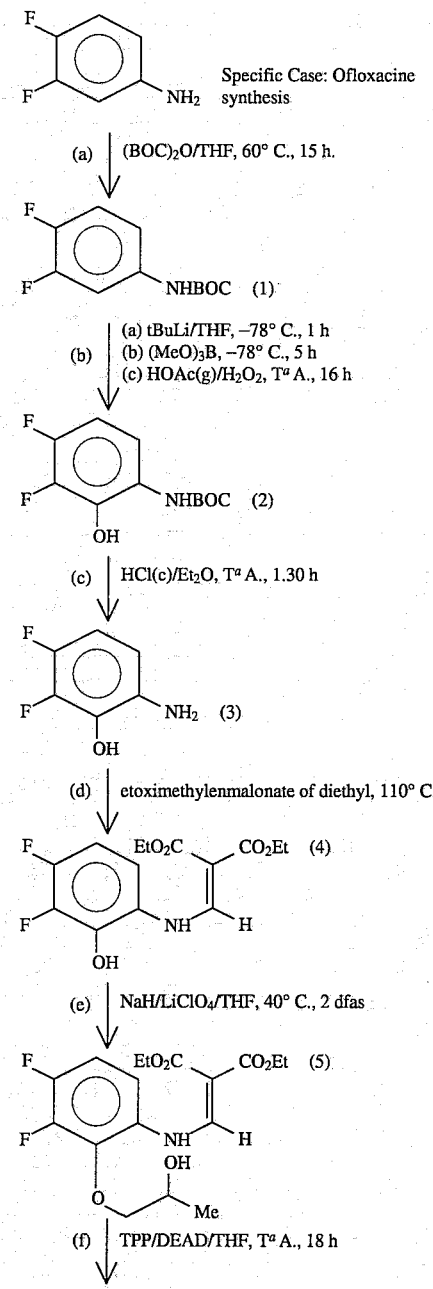

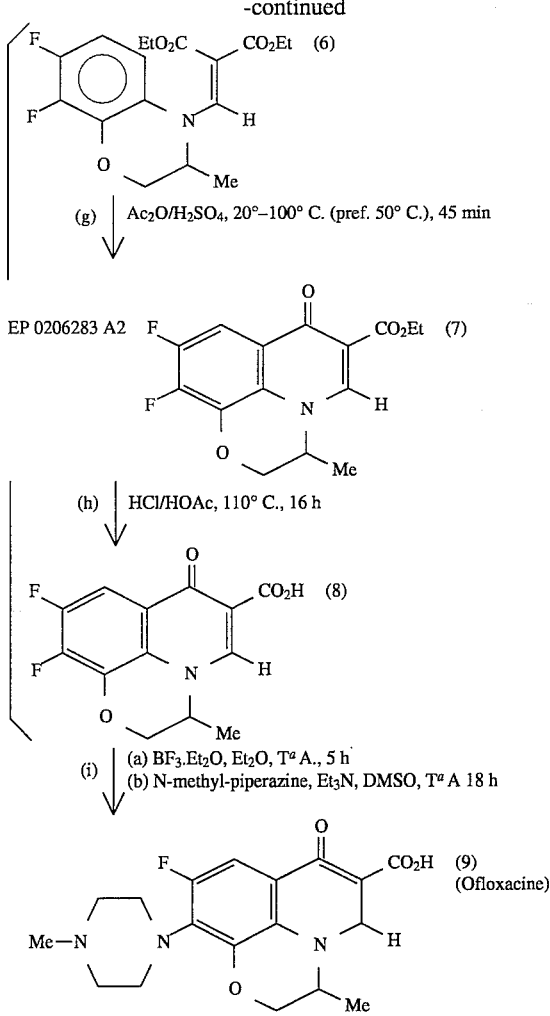

where Y represents an alcoxyl group.

The reaction can be carried out in the absence or in the presence of inert solvents such as n-hexane or other similar ones.

The reaction can be performed within a temperature ranging between 90° and 180° C. in the absence of a solvent, or at temperatures close to the boiling temperature of the solvent in the presence of solvents.

The preferred way to perform this stage implies the use of n-heptane as solvent and the heating of the n-heptane at counterflow temperature.

Step e. Formation of the oxibenzene derivative (II) through the opening of epoxides of formula

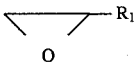

where

R$_1$ is the one defined above (in the specific case shown in the reaction scheme, R$_1$ is methyl).

It consists of a reaction in which a catalyzed opening of the epoxide is produced in a mild temperature and adequate catalyst proportions. In general terms, this step can be performed at a temperature ranging between 0° and 60° C., preferably between 20° and 50° C., and even more preferably at 40° C., in the presence of a catalyst which can be a Lewis acid such as the boric trifluoro, zinc bromide, magnesium bromide, lithium perchlorate, and in the presence of a base preferably sodium hydride. The molar ratios of the reactives (initial product/catalyst/epoxide) involved in this step can be 1–1.5/2–6/1–5–3, respectively.

In this reaction step, if the optically pure and adequate chiral epoxide is used, the formation of the enantiomerically pure compound [5] is obtained and, following the synthetic way, it offers the two Ofloxazine enantiomers. Therefore, this method does not require a resolution stage. In general, this reaction step can be performed in an aprotic solvent.

Step f. The cycling of the oxibenzene derivative [5] is performed stereoselectively by using triphenylphosphine (TPP) and ethyl azodicarboxylate as reactives with an inert, little polar and organic solvent such as the tetrahydrofurane, at a temperature ranging between 0° and 60° C., preferably between 20° and 30° C., and even better at a room temperature, for a period of time of 12–30 hours, preferably 18 hours.

Steps g, h. These are described in the application for the European Patent No. EP 0206283 A2 which enables to obtain the chinolone core and the Ofloxazine. Additionally, it is possible to obtain chinoline derivatives (optionally replaced in position 7 by piperazine) from the methylenmalonate derivatives following the Gould-Jacobs sequence (thermal or catalysed cycling followed by the ester hydrolysis and the replacement of fluorine by piperazine) [Hayakawa et al., *Chem. Pharm. Bull.*, 1984, 32, 4907; Koga et al., *J. Med. Chem.*, 1980, 23, 1358; Albrecht R., *prog. Drug. Res.*, 1977, 21, 9–104].

Step i. The 9-fluoro-3-methyl-7-oxo-2,3 dihydro-7H-pyrid[1,2,3-de]benzoxazine-6-carboxylic acid [8] obtained is subject to N-methylpiperazine in an adequate polar inert solvent such as DMSO (dimethylsulphoxide), or aceto nitrile, preferably DMSO, at a temperature ranging between 50° and 150° C., preferably at a temperature ranging between 100° and 120° C. and, optionally, in the presence of a base such as triethylamine, the Ofloxacine [9] can be obtained which can be in a racemic form if the propylene (R,S)-oxide or its pure enantiomer forms have been used such as, for instance, the 3-(S)- form or Levofloxazine if the Propylene (R)-oxide has been used.

Step a. The protection of the amino group of the 3,4-difluoroaniline is carried out through an adequate protecting group such as (B=C)$_2$O (ditertbutyldicarbonate) in little polar solvents such as ethers, chlorinated solvents and similar ones at temperatures ranging between 30° and 100° C. The BOC group acts not only as a blocking agent but also to achieve an "ortho-directing" effect which the amino group does not have as such. Additionally, this stage can also be advantageously and preferably carried out using n-heptane as solvent and heating it at the counterflow temperature of the solvent.

Step b. The execution of this step calls for a strong base, generally alkyllithium to provoke the orthometalation which is completely regioselective at position 2 and low temperatures. The sequence continues by adding trimethyl borate also at low temperatures. In general terms, this step can be carried out at a temperature ranging between –50° and –90° C., preferably at –78° C. Subsequently, the oxidation of the arylborate in an acidic medium with oxygenated water enables to obtain the relevant phenol [2]. In the reaction, inert and poor polar solvents are used.

Step c. The deprotection of the amino group is carried out in a conventional way—known as per se—for instance, through a treatment with diluted acids.

Step d. This step is carried out through the reaction of 6-amino-2,3-difluorophenol [3] with a compound of the type:

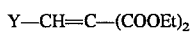

7

Alternatively, this step (i) can be advantageously performed, in the absence of a base, by using DMSO as solvent, and heating it at a temperature of approx. 100° C. for two hours.

The invention is profusely illustrated by means of the following examples, it being understood that they do not limit the scope of this invention.

EXAMPLE 1

Synthesis of 3,4-difluoro-N-(tert-butoxicarbonyl)aniline [1]

Method 1

2,42 g (11.1 mmol) of dicarbonate ditertbutyl are added to a solution of 1.30 g (10.1 mmol) of 3,4-difluoroaniline in 10 ml of THF. The mixture is heated at 60° C. for 15 hours, the solvent is eliminated and the brown solid obtained is solved in ethyl acetate (15 ml) and is washed several times with 1% HCl (2×3 ml) and 5% NaHCO₃ 5% (2×3 ml). The organic stage is dried with MgSO₄ and the solvent is eliminated. 2,28 g (99%) of the product are obtained [1] which is recrystallised with hexane, finally obtaining 2,24 g (97%) of pure compound [1].

Method 2

8,89 g (40,79 mmol) of dicarbonate ditertbutyl are added to a solution of 5,00 g (38.85 mmol) of 3,4-difluoroaniline in 40 ml of n-heptane. The reaction mixture is heated at counterflow for 3.5 hours. Then, it is cooled at room temperature until a precipitate appears which is filtered in vacuum and washed with 20 ml of n-heptane. 8.7 g (98%) of pure 3,4-difluoro-N-(tert-butoxycarbonyl)-aniline [1] is obtained.

Spectroscopic and physical data m.p. 135°–137° C.; $^1$H NMR (CDCl₃) δ: 7.43 (ddd, 1H, J=12.3, 7.5 and 2.6 Hz, ArH), 7.05 (m, 1H, ArH), 6.90 (m, 1H, ArH), 6.48 (s wide, 1H, NH) and 1.52 (s, 9H, $^t$Bu) ppm; IR (nujol) v: 3300, 2880, 2800, 1690, 1610, 1430, 1390, 1370, 1290 and 1170 cm$^{-1}$; MS m/e: 229 (M⁺, 10), 173 (37), 129 (43), 101 (13), 86 (18), 84 (22), 59 (20), 57 (100); Analysis calculated for $C_{11}H_{13}F_2NO_2$: C, 57.64; H, 5.67; N, 6.11; found C, 57.63; H, 5.56; N, 6.06.

EXAMPLE 2

Synthesis of 6-tert-butoxycarbamoyl-2,3-difluoro-phenol [2]

16.4 ml (26.24 mmol) of a solution 1.6M 'BuLi' in hexane are added slowly at −78° C. and under an argon atmosphere to 3.0 g (13.12 mmol) of the compound [1] solved in 45 ml of anhydrous THF. The reaction mixture is kept at −78° C. for 1 hour and, afterwards, 2.25 ml (19.68 mmol) of trimethyl borate are slowly added. After 5 hours at −78° C., 1.2 ml of glacial acetic acid are added, and then—drop by drop–3 ml of H₂O₂ at 30%. The reaction mixture is heated at room temperature and kept agitating the overnight. 15 ml of H₂O are added. The organic layer is separated and the aqueous one is extracted with CH₂Cl₂ (3–15 ml). The organic layers combination is dried on MgSO₄ and the solvent is eliminated. The gross product of the reaction is purified by means of FLASH chromatography (ethyl:hexane acetate 1:15), thus obtaining 2.85 g (89%) of the product [2].

Spectroscopic and physical data $^1$H NMR (CDCl₃) δ: 8.15 (s wide, 1H, OH); 7.01 (ddd, 1H, J=9.2, 5.1 and 2.3 Hz, ArH), 6.73 (s wide, 1H, NH), 6.65 (m, 1H, ArH) and 1.53 (s, 9H, $^t$Bu) ppm.

8

EXAMPLE 3

Synthesis of 6-amino-2,3 difluoro-phenol [3]

60 ml of concentrated HCl, at room temperature and subject to magnetic agitation, are added to a solution of 2.85 g (11.66 mmol) of the compound [2] in 126 ml of ethylic ether. After 90 minutes, a solution of NaOH up to pH=6 is slowly added to the reaction mixture. The organic layer is separated and the aqueous one is extracted with more ethylic ether (3×25 ml). The combined ether extracts are washed with water (2×15 ml), dried on MgSO₄ and the solvent is eliminated. 1.45 g (86%) of product [3] are obtained which can be used in the following stage without the need of a previous purification.

Spectroscopic and physical data $^1$H NMR (CDCl₃): 6.54 (m, 1H, ArH); 6.42 (ddd, 1H, J=8.8, 4.8 and 1.9 Hz, ArH) and 4.2 (s wide, 2H, NH) ppm.

EXAMPLE 4

Synthesis of diethyl (3,4-difluoro-2-hydroxyaniline)-methylenmalonate [4]

Method 1

A mixture of 1.45 g (10.02 mmol) of the compound [3] and 2.03 ml (10.02 mmol) of diethyl ethoxymethylenmalonate of diethyl is heated at 110° C. dor 60 minutes. Then it is cooled at room temperature and hexane added until a precipitate is obtained which is filtered in vacuum and washed with more hexane. 2.60 g (80%) of the product [4] are obtained and it does not need to be subject to a subsequent purification treatment.

Spectroscopic and physical data $^1$H NMR (CDCl₃) δ: 11.07 (d, 1H, J=13.8 Hz, NH); 8.47 (d, 1H, J=13.8 Hz, HC═C); 6.94 (m, 1H, ArH); 6.6 (s wide, 1H, OH); 6.74 (m, 1H, ArH); 4.33 (c, 2H, J= 7.1 Hz, OCH₂); 4.26 (c, 2H, J=7.1 Hz, OCH₂); 1.38 (t, 3H, J=7.1 Hz, CH₃) and 1.33 (t, 3H, J=7.1 Hz, CH₃) ppm.

Method 2

13.44 ml (66.34 mmol) of diethyl ethoxymethylenmalonate of are added to a solution of 9.6 g (66.34 mmol) of 3,4-difluoro-2-hydroxy-aniline [3] in 50 ml of n-heptane. The reaction mixture is reflux heated for 1 hour and then cooled at room temperature until a precipitate is obtained which is filtered at vacuum and washed with 20 ml of n-heptane. 17.5 g (81%) of diethyl (3,4-difluoro-2-hydroxyaniline)-methylenmalonate [4] are obtained and it does not need to be subject to a subsequent purification treatment.

EXAMPLE 5

Synthesis of diethyl[3,4-difluoro-2-(2-hydroxypropoxy(aniline]-methylenmalonate [5]

2,9 mgr (0,06 mmol) of HNa at 60%, 161 mgr (1,26 mmol) of LiClO₄ anhydrous and 51 ml (0,32 mmol) of propylene oxide are added to a solution of 100 mgr) 0,32 mmol) of the compound [4] in 0,33 ml of THF. The reaction mixture is heated at 40° C. for two days and then 2 ml of water are added. The aqueous layer is extracted with ACOEt, ethyl acetate, (2×5 ml). The combination of the organic layers is dried with MgSO₄ and the solvent is eliminated thus obtaining 77 mgr (65%) of the desired product [5].

Spectroscopic and physical data

¹HRMN (CDCl₃) δ: 11.44 (d, 1H, J=13.8 Hz, NH); 8.47 (d, 1H, J=13.8 Hz, HC=C); 7.1–6.8 (m, 2H, ArH); 4.4–3.9 (m, 7H, CH₂CH and CH₃CH₂O); 1.27 (d, 3H, J=6.7 Hz, CH₃CH) and 1.37 (t, 3H, J=7.2 Hz, CH₃CH₂O).

EXAMPLE 6

Synthesis of diethyl (7,8-difluoro-3-methyl-2,3-dihydro-4H-[1,4]benzoxazine-4-il)methylenmalonate [6]

Slowly and with the help of a perfuser, at room temperature, under an argon atmosphere and for 18 hours, a solution of 47 microliters of diethyl axodicarboxylate (0,26 mmol) in 0.5 ml of THF is added to a solution of 50 mg (0.13 mmol) of the compound [5] and 48 mg of triphenylphosphine (0.26 mmol) in 1.2 ml of anydrous THF. Then the solvent is eliminated at a reduced pressure and the residue is treated with ethylic ether until a precipitate is obtained (formed by diethyl hydrazocarboxylate and triphenylphosphine oxide) which is separated by filtration. The ether solution is concentrated until an oil is obtained which is purified by flash chromatography (ethyl:hexane acetate 1:5) thus obtaining 30 mg (79%) of the product [6] pure.

Spectroscopic and physical data
¹HRMN (CDCl₃) δ: 11.44 (d, 1H, J=13.8 Hz, NH); 8.47 (d, 1H, J=13.8 Hz, HC=C); 7.1–6.8 (m, 2H, ArH); 4.4–39 (m, 7H, CH₂CH and CH₃CH₂O); 1.27 (d, 3H, J=6.7 Hz, CH₃CH) and 1.37 (t, 3H, J=7.2 Hz, CH₃CH₂O)

EXAMPLE 7

Synthesis of ethyl 9,10-difluoro-3-methyl-7-oxo-2,3 dihydro-7H-pyrid (1,2,3-de)benzoxazine-6-carboxylate [7]

Slowly and under magnetic agitation, 0.15 ml of a mixture of acetic anhydride and sulfuric acid at a ratio of 1:2 are added to a solution, cooled at 0° C., of 30 mg (0.08 mmol) of the product [6] in 0.06 ml of acetic anhydride. The reaction mixture is heated at 50° C. for 45 minutes. Then ice is added to the mixture and the mixture is vigorously agitated until a large quantity of precipitate is obtained. The solid is filtered and washed several times with ethyl ether. 19 mg (73%) of product [7] are obtained which can be used in the following stage without the need of a previous purification.

Spectroscopic and physical data
¹H NMR (CDCl₃) δ: 8.41 (s, 1H, HC=C); 7.85 (dd, 1H, J=10.8 and 7.8 Hz, ArH); 4.5–4.3 (m, 5H, CH₂CH and CH₃CH₂O); 1.61 (d, 3H, J=6.7 Hz, CH₃CH) and 1.41 (t, 3H, J=7.2 Hz, CH₃CH₂O) ppm.

EXAMPLE 8

Synthesis of 9,10-difluoro-3-methyl-7-oxo-2,3 dihydro-7H-pyrid(1,2,3-de)benzoxazine-6-carboxylic acid [8]

A solution of 19 mg (0.06 mmol) of the ester [7] in 0.27 ml of a mixture of concentrated hydrochloric acid and acetic acid at a ratio of 1:4 respectively is heated at 110° C. for 16 hours. Then it is cooled at room temperature until a large quantity of precipitate is obtained. The solid is filtered and 11 mg (68%) of product [8] are obtained which can be used in the following stage without the need of a previous purification.

Spectroscopic and physical data
¹H NMR (CF₃CO₂D) δ: 9.32 (s, 1H, HC=C); 8.01 (dd, 1H, J=9.2 and 7.1 Hz, ArH); 5.3–4.4 (m, 3H, CH₂CH) and 1.75 (d, 3H, J=6.9 Hz, CH₃CH) ppm.

EXAMPLE 9

Synthesis of 9-fluoro-3-methyl-10-(4-methyl-1-piperazinyl)-7-oxo-2,3 dihydro-7H-pyrid(1,2,3-de) (1,4)-benzoxazine-6-carboxylic acid [9]

Method 1

14.3 g of the compound [8] are suspended in 600 ml of ethyl ether and 70 ml of trifluoride of etherate diethyl boron, and kept agitating at room temperature for 5 hours. The floating liquid is eliminated by decantation and added to the ethylic ether residue and filtered. The solid is washed with ethyl ether and dried.

The product obtained is solved in 100 ml of DMSO, and 14.2 ml of triethylamine and 7.3 ml of 4-methyl-piperazine are added to the solution. The mixture is agitated for 18 hours at room temperature and the solvent is eliminated by distillation. Ethyl ether is added to the residue and filtered. The yellow powder obtained is suspended in 400 ml of methanol at 95%, and then 25 ml of triethylamine are added. The mixture is reflux heated for 25 hours and the solvent is eliminated by distillation at reduced pressure. The residue is solved in 500 ml of chlorhydric acid at 10% and washed three times with chloroform. The pH of the washed solution is adjusted at 11 with an aqueous solution of 4N sodium hydroxide and then it is taken to pH 7.3 with 1N HCL.

The solution is extracted three times with portions of 2 liters of chloroform and the combined extract is dried on sodium sulphate. The chloroform is eliminated by distillation and the resulting crystals will be recrystallised from ethanol/ethylic ether to obtain 12 g of the product [9] (m.p. 226°–230° C. with decomposition).

Method 2

46 ml (0.42 mmol) of N-methylpiperazine are added, at room temperature, to a solution of 70 mg (0.21 mmol) of 9,10-difluoro-2,3dihydro-3-methyl-7-oxo-7H-pyrid(1,2,3-de) (1,4)-benzoxazine-6-carboxylic acid [8] in 1.5 ml of DMSO. The solution is heated at 100° C. for 2 hours. Then the solvent is eliminated at reduced pressure and 2 ml of ethanol are added to the bulk of the reaction thus obtaining a precipitate that, after filtering, provides 75 mg (79%) of the desired product, Ofloxacina or 9-fluoro-2,3dihydro-3-methyl-10-(4-methyl-1-piperazynil)-7-oxo-7H-pyrid(1,2,3-de) (1,4)-benzoxazine-6-carboxylic acid [9] (m.p. 226°–230° C. with decomposition).

We claim:
1. A process to obtain the 3-(S)-isomer of Ofloxazine (Levofloxazine) characterized in that
 (i) diethyl(3,4-difluoro-2-hydroxyaniline)methylenmalonate is reacted with (R)-oxide of propylene in an adequate solvent and in the presence of a base and an adequate catalyst to obtain the diethyl[3,4-difluoro-2-(2-hydroxypropoxy)aniline]methylenmalonate that
 (ii) is reacted with triphenylphosphine and diethyl azodicarboxilate to obtain the diethyl(7,8-difluoro-3(S)-methyl-2,3-dihydro-4H-[1,4]benzoxazine-4-yl)methylenmalonate that
 (iii) is cycled by adding the acetic anhydride in an acid medium to perform the ethyl 9,10-difluoro-3-(S)-methyl-7-oxo-2,3-dihydro-7H-pyrid[1,2,3-de]benzoxazine-6-carboxilate that, then,
 (iv) it is subject to an acid hydrolysis to obtain the relevant 9,10-difluoro-3-(S)-methyl-7-oxo-2,3-dihydro-7H-pyrid[1,2,3-de]benzoxazine-6-carboxilic acid that
 (v) treated with N-methylpiperazine so that the 3-(S)- of Ofloxacine (Levofloxacine) isomer is obtained.

2. A process for preparing Ofloxazine of formula

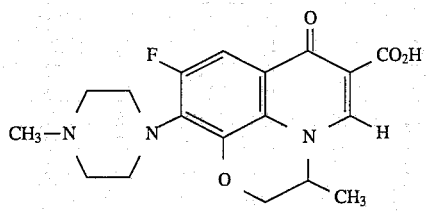
(A)

comprising:

(1) preparing benzoxazine derivatives of general formula (I)

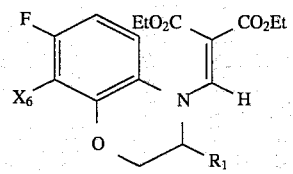
(I)

where

R₁ is H, an alkyl radical of up to 6 carbon atoms, preferably methyl, an alkenyl radical of up to 6 carbon atoms or an aryl group; and Xb is an halogen atom, preferably fluorine; by a method comprising the following steps:

(a) preparing oxibenzene derivatives of general formula (II)

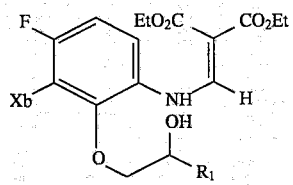
(II)

where

R₁ is H, an alkyl or alkenyl radical of up to 6 carbon atoms, or an aryl group; and Xb is an halogen atom, by reacting a compound of general formula (III)

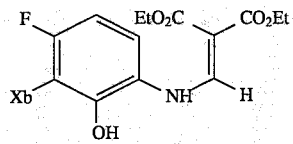
(III)

with an epoxide of general formula

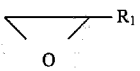

where Xb and R₁ have the meaning described above, in an adequate solvent, in the presence of a base and a catalyst, (b) cycling an oxibenzene derivative of general formula (II), prepared by the method of step (a), by reacting with triphenylphosphine and ethyl azodicarboxylate with the adequate solvent, to obtain the benzoxazine derivatives of formula (I), and (2)(i) reacting a benzoxazine of formula (I), where Xb is F and R₁ is methyl, obtained by the method of step (1), with acetic anhydride, in an acidic medium at a temperature ranging between 20° and 100° C., to obtain a chinolone of formula (7)

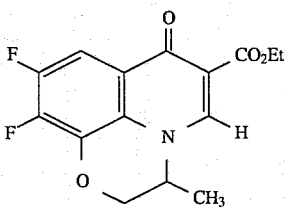
(7)

(ii) hydrolyzing, in an acidic medium, the chinolone (7) previously obtained, thus obtaining an acid of formula (8)

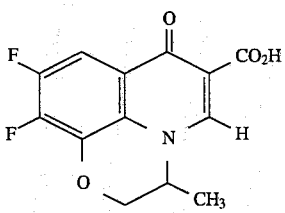
(8)

and (iii) reacting the acid (8) previously obtained with N-methylpiperazine in an adequate polar solvent, at a temperature ranging between 50° and 150° C., optionally in the presence of a base, to obtain Ofloxazine of formula (A).

* * * * *